US012514732B2

(12) United States Patent
Duke et al.

(10) Patent No.: US 12,514,732 B2
(45) Date of Patent: Jan. 6, 2026

(54) ORTHOTIC KNEE CONTROL DEVICE FOR PROVIDING EASE OF MOVEMENT

(71) Applicant: Blatchford Products Ltd, Basingstoke (GB)

(72) Inventors: Chris Duke, Basingstoke (GB); Mir Saeed Zahedi, London (GB); Graham Harris, Basingstoke (GB)

(73) Assignee: BLATCHFORD PRODUCTS LTD, Basingstoke (GB)

( * ) Notice: Subject to any disclaimer, the term of this patent is extended or adjusted under 35 U.S.C. 154(b) by 165 days.

(21) Appl. No.: 18/360,443

(22) Filed: Jul. 27, 2023

(65) Prior Publication Data

US 2023/0372137 A1 Nov. 23, 2023

(30) Foreign Application Priority Data

Jul. 29, 2022 (EP) .................................... 22187950

(51) Int. Cl.
*A61F 5/01* (2006.01)

(52) U.S. Cl.
CPC .... *A61F 5/0125* (2013.01); *A61F 2005/0169* (2013.01); *A61F 2005/0179* (2013.01)

(58) Field of Classification Search
CPC .... A61F 5/0106; A61F 5/0111; A61F 5/0585; A61F 5/05858; A61F 2005/0132; A61F 5/0102; A61F 5/0123; A61F 5/0125; A61F 2005/0169; A61F 2005/0179; A61F 2005/0155; A61G 13/123; A61H 1/024; A61H 1/0255; A61H 1/0237
See application file for complete search history.

(56) References Cited

U.S. PATENT DOCUMENTS

| | | | | |
|---|---|---|---|---|
| 3,799,159 A * | 3/1974 | Scott | A61F 2/68 | 602/26 |
| 2015/0051527 A1* | 2/2015 | Potter | A61F 5/0125 | 602/16 |
| 2021/0106441 A1* | 4/2021 | Naseri | A61F 2/68 | |
| 2022/0409416 A1* | 12/2022 | Sacherer | A61F 5/0125 | |

* cited by examiner

*Primary Examiner* — Ophelia A Hawthorne

(57) ABSTRACT

Embodiments herein discloses an orthotic knee control device providing ease of movement. The orthotic knee control device includes a hydraulic piston connected with a hydraulic chamber, accumulator spring(s) connected with an accumulator chamber, a non-return valve connected in between the hydraulic chamber and the accumulator chamber. The non-return valve allows the flow of an oil from the accumulator chamber to the hydraulic chamber and does not allow the flow of the oil from the hydraulic chamber to the accumulator chamber. Further, the orthotic knee control device includes a motorized valve connected between the hydraulic chamber and the accumulator chamber. Further, the accumulator springs apply pressure to the hydraulic piston, to resist flexion of a knee joint and to aid extension of the knee joint.

18 Claims, 7 Drawing Sheets

ORTHOTIC KNEE CONTROL DEVICE FOR PROVIDING EASE OF MOVEMENT

PRIORITY DETAILS

The present application is based on, and claims priority from a European Application Number EP22187950.5 filed on 29 Jul. 2022, the disclosure of which is hereby incorporated by reference herein.

FIELD

The present disclosure relates to an orthotic knee control device, and more specifically to the orthotic knee control device with a hydraulic damping and an extension bias for providing ease of movement of a user.

BACKGROUND

Generally, an orthotic knee control device is worn over the knee of an intact limb to support the function of a natural knee joint. The orthotic knee control device is based on hinged joints that lock to support the intact limb during walking and unlocks for sitting. However, the orthotic knee control device does not provide natural knee joint flexion during walking and controlled support during sitting or descending stairs due to the need to manually lock and unlock the orthotic knee control device.

In some conventional methods and devices, the orthotic knee control device is provided with hydraulic controls to offer natural knee joint flexion during walking and controlled support for sitting or descending stairs. However, orthotic devices with hydraulic damper control systems generate resistance opposing motion. When a hydraulically controlled orthotic knee device is worn by a user with limited knee joint power, the resistance in the direction of the motion leads to difficulties in achieving extension movement of their knee joint throughout swing phase, especially towards the end of the swing phase prior to heel contact.

Technical Problem

The technical problems when a hydraulic control is used as a damper in a knee orthosis is that the resistance opposes the motion of the user.

The conventional orthotic knee control device has high risk of tripping, no stumble recovery, no support during high flexion activities includes, but not limited to, stair descent and sitting. Further, the conventional orthotic device is not suitable for the users with weakness of a quadriceps.

The technical problems in a conventional microprocessor-based orthotic knee control device is that the conventional microprocessor-based orthotic knee control device is bulky in nature thus difficult to wear under clothing.

Thus, it is desired to address the above mentioned disadvantages or other shortcomings or at least provide a useful alternative to reduce or remove the resistance in the direction of the motion.

Technical Solution

The principal object of the embodiments herein is to provide an orthotic knee control device providing ease of movement. The orthotic knee control device provides variable resistance during flexion of a knee joint aiding knee extension, reducing the risk of tripping, providing stumble recovery and support during activities that involves large knee flexion angles includes, but not limited to, stair descent, sitting and the like.

Another object of the embodiments herein is to provide motion control in an extension direction, variable control of extension damping during swing, and stance extension adjustments by using a motorized valve to overcome weakness of the quadriceps.

Yet another object of the embodiments herein is to provide bias in extending the knee joint utilizing pressure from accumulator springs to support users with lower limb paralysis.

Yet another object of the embodiments herein is to provide a pre-set resistance that is adjusted to user's specific requirements, the pre-set resistance is selected by the user depending on the environment or activity including cycling, sitting, standing and walking.

Yet another object of the embodiments herein is to increase flexion control and extension assistance during fast walking, sitting, and stair descent by varying or adjusting stiffness of the accumulator springs.

SUMMARY

Accordingly the embodiment herein is to provide an orthotic knee control device providing ease of movement. The orthotic knee control device includes a hydraulic piston connected to a hydraulic chamber, accumulator springs connected to an accumulator chamber, and a non-return valve connected between the hydraulic chamber and the accumulator chamber. The non-return valve allows the flow of an oil from the accumulator chamber to the hydraulic chamber and does not allow the flow of the oil from the hydraulic chamber to the accumulator chamber. Further, the orthotic knee control device includes a motorized valve connected between the hydraulic chamber and the accumulator chamber. The motorized valve controls the flow of oil based on one or more sensors to provide appropriate resistance for the user, this ensures that following maximum flexion, the motorised valve can move to a relatively high resistance to provide support to the user when the user stumbles while the Non-return valve allows free extension. Further, the accumulator springs apply pressure to the hydraulic piston, to resist knee joint flexion and aid in extension of the knee joint.

In an embodiment, the oil flows from the hydraulic chamber to the accumulator chamber through the motorized valve when a user flexes the knee joint. Further, the accumulator springs are compressed when the user flexes the knee joint.

In an embodiment, the oil flows from the accumulator chamber to the hydraulic chamber through one or more of the motorized valves and the non-return valve when the user extends the knee joint.

In an embodiment, the oil flows from the accumulator chamber to the hydraulic chamber through the motorized valve provides one or more of: motion control in an extension direction, control of extension damping during a swing and a stance extension.

In an embodiment, the pressure from the accumulator springs on the hydraulic piston produces a bias extending the knee joint.

In an embodiment, the orthotic knee control device includes an override button, that allows the oil to flow from the accumulator chamber to the hydraulic chamber or from the hydraulic chamber to the accumulator chamber without using one or more of the motorized valves and the non-return valve. In an embodiment, the override button is used by the user when one or more of the motorized valves and the non-return valve is jammed or power failure or when the user wants to flex the knee quickly (for example: during sitting).

In an embodiment, the override button releases the knee joint to a pre-set resistance that is appropriate to the user or an environment. Further, the pre-set resistance selected by the user depends on the environment or actions of the user including but not limited to cycling, sitting, and walking.

In an embodiment, one or more override buttons comprises plurality of positions for different levels of resistance.

In an embodiment, the accumulator springs have a stiffness corresponding to a deflection. The deflection is low for an initial knee flexion resulting in stiffness of the accumulator springs to be low. Further, increase in knee flexion, increases accumulator spring deflection and corresponding stiffness improving flexion control and extension assistance including but not limited to fast walking, sitting, and stair descent.

In an embodiment, the accumulator springs includes a primary spring and a secondary spring. The primary spring applies pressure to the hydraulic piston when a flexion angle of the knee joint is lesser than a threshold. The secondary spring applies pressure to the hydraulic piston when the flexion angle of the knee joint is greater than the threshold.

In an embodiment, the flexion angle is proportional to a compression rate of the accumulator springs.

In an embodiment, the motorized valve controls the flow of the oil based on one or more sensors including but not limited to a pressure sensor, a foot force sensor, and kinematic sensors. Further, the one or more sensors determines includes, but not limited, to joint angles, velocities, and accelerations of the knee joint or a thigh segment.

In an embodiment, the motorized valve is adjusted to provide including, but not limited to, the required level of stance control, to provide free swing, and make knee resistance suitable for sitting and stair descent.

In an embodiment, the orthotic knee control device provides ease of movement without the usage of motorized valve.

In an embodiment, the accumulator springs are interchangeable springs that are interchanged with other springs based on user requirements to provide a degree of compression. Further, the degree of compression is achieved by modifying the pitch of coils in the accumulator springs and adding one or more secondary springs along with the primary spring.

In an embodiment, the degree of compression is modified by adjusting the pre-load of the accumulator springs.

In an embodiment, the accumulator springs provide variable resistance to the flexion.

In an embodiment, the flexion angle and hydraulic piston travel velocity are considered for fine movements of the user.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein, and the embodiments herein include all such modifications.

BRIEF DESCRIPTION OF THE FIGURES

For a more complete understanding of the present disclosure and its advantages, reference is now made to the following description taken in conjunction with the accompanying drawings, in which like reference numerals represent like parts.

DETAILED DESCRIPTION OF INVENTION

Figure 1:
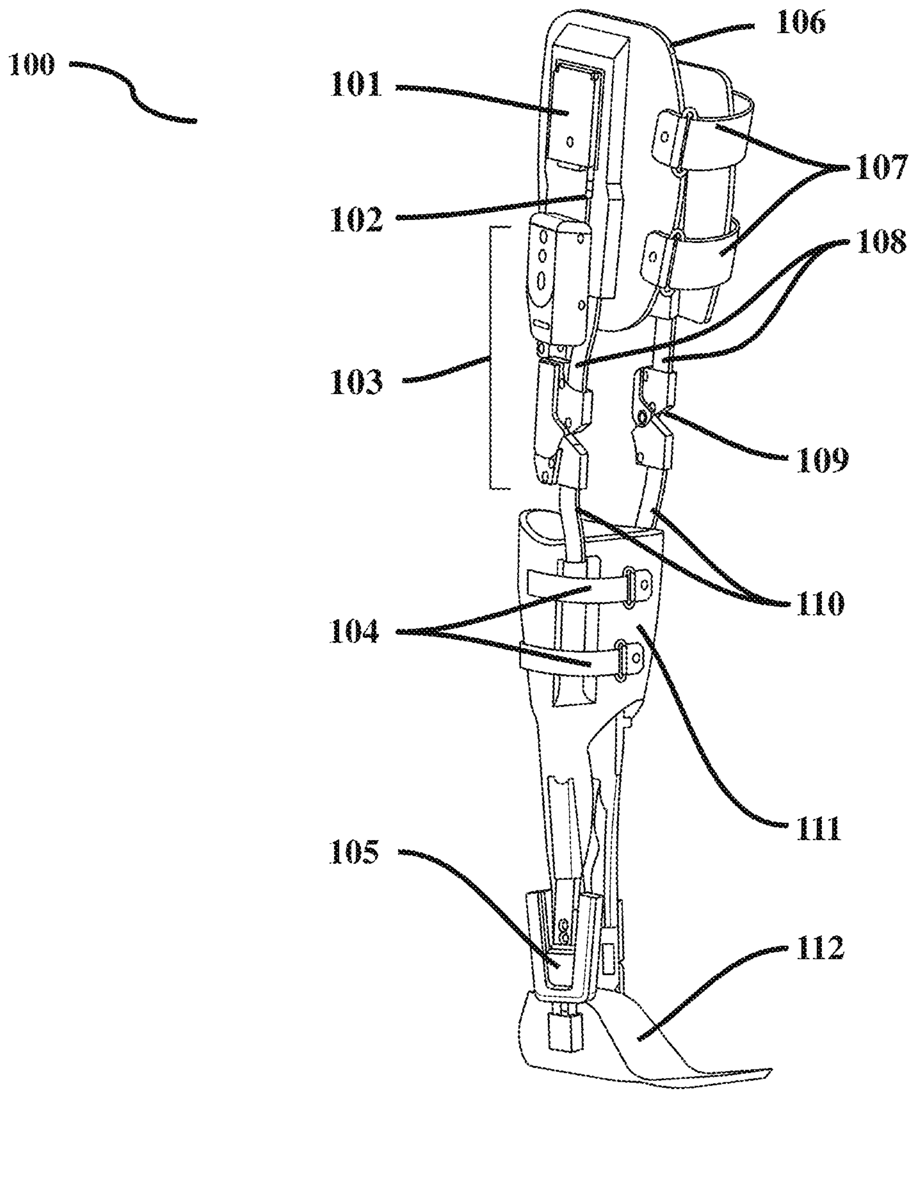
FIG. 1 is a schematic diagram illustrates a structure of an orthosis with an orthotic knee control device, according to the embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term “or” as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

As is traditional in the field, embodiments may be described and illustrated in terms of blocks which carry out a described function or functions. These blocks, which may be referred to herein as managers, units, modules, hardware components or the like, are physically implemented by analog and/or digital circuits such as logic gates, integrated circuits, microprocessors, microcontrollers, memory circuits, passive electronic components, active electronic components, optical components, hardwired circuits and the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the disclosure. Likewise, the blocks of the embodiments may be physically combined into more complex blocks without departing from the scope of the disclosure.

The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings. Although the terms first, second, etc. may be used herein to describe various elements, these elements should not be limited by these terms. These terms are generally only used to distinguish one element from another.

Accordingly the embodiment herein is to provide an orthotic knee control device that provides ease of movement. The orthotic knee control device includes a hydraulic piston connected to a hydraulic chamber, accumulator springs connected to an accumulator chamber, and a non-return valve connected between the hydraulic chamber and the accumulator chamber. The non-return valve allows the flow of an oil from the accumulator chamber to the hydraulic chamber and does not allow the flow of the oil from the hydraulic chamber to the accumulator chamber. Further, the orthotic knee control device includes a motorized valve connected between the hydraulic chamber and the accumulator chamber. The motorized valve controls the flow of oil based on one or more sensors. Further, the accumulator springs apply pressure to the hydraulic piston, to resist flexion of a knee joint and to aid extension of the knee joint.

The conventional methods and devices are custom-built devices that need to be tuned to a specific user's impairment. However, tuning to the specific user impairment is difficult, consumes time, optimised for a limited range of functions and does not provide automatic customization based on the situation. Unlike the conventional methods and devices, the proposed orthotic knee control device is rapidly customised to the specific user impairment, and optimized for a range of functions and situations.

The conventional microprocessor-based orthotic knee control devices are bulky and hence the conventional microprocessor-based orthotic knee control devices are difficult to wear under clothing. Unlike conventional methods and devices, the proposed orthotic knee control device is slim and more easily worn under clothing.

Referring now to FIGS. 1 through 4D, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged orthotic device.

FIG. 1 is a schematic diagram illustrating a structure of an orthosis (100) with an orthotic knee control device (103), according to the embodiments as disclosed herein.

Referring to the FIG. 1, the orthosis (100) are external appliances worn to correct extremity alignment, to achieve mobility, to support an intact limb and to support weak or ineffective joints or muscles. In FIG. 1, the orthosis (100) includes a battery module (101), a connecting cable (102), the orthotic knee control device (103), lower leg straps (104), an ankle module (105), a thigh shell (106), thigh straps (107), upper knee side-bars (108), a follower joint (109), lower knee slide bars (110), a lower leg shell (111) and a foot shell (112). The follower joint (109) provides additional support and control for the orthosis, alternatively the knee control device is mounted without the follower joint (109) depending on the level of support required.

The orthotic knee control device (103) in the orthosis (100) supports the intact limb during walking, sitting and other movements. Further, the orthotic knee control device (103) is connected with the battery module (101).

Figure 2:
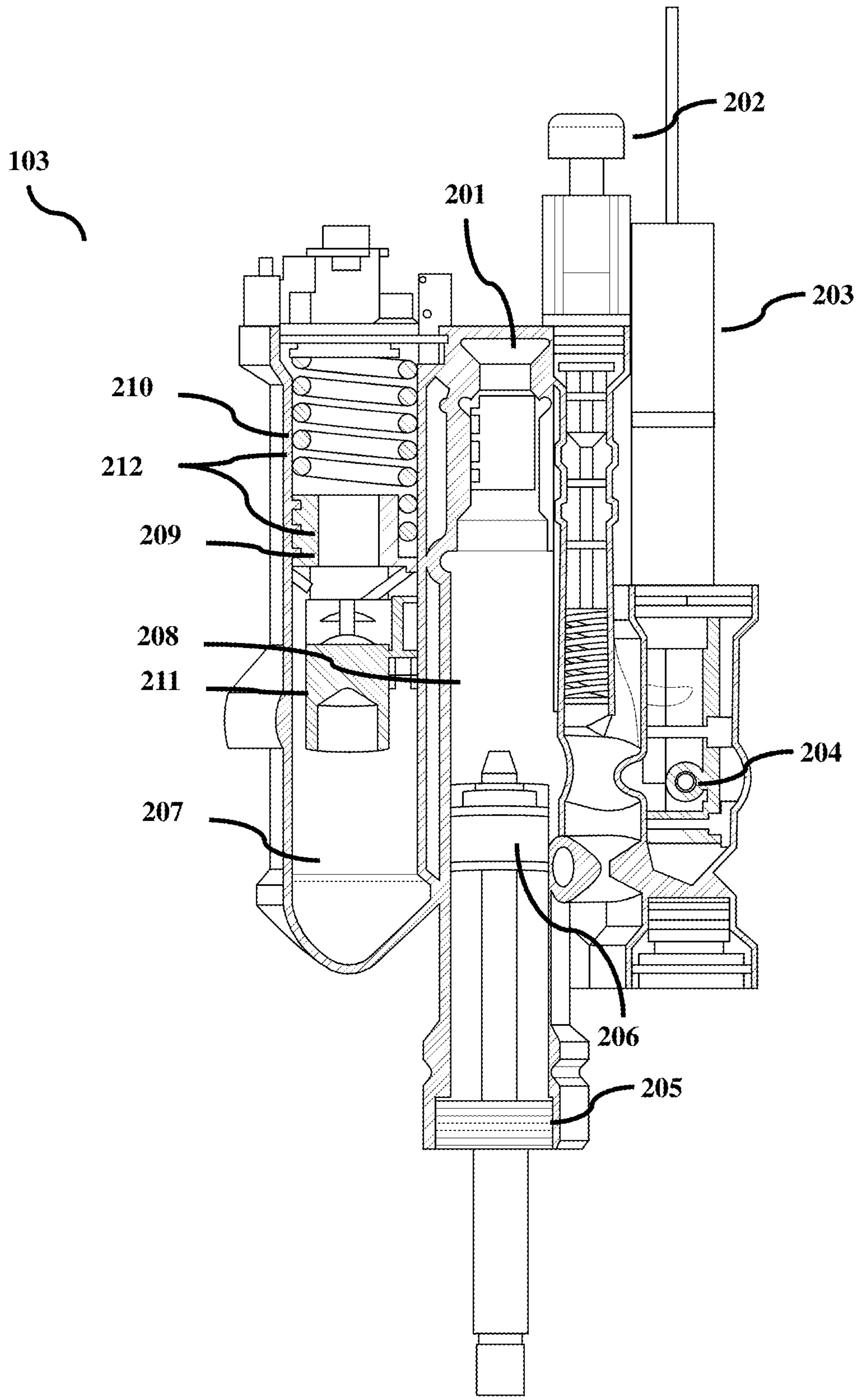
FIG. 2 is a section view diagram illustrating the orthotic knee control device, according to an embodiment as disclosed herein.

FIG. 2 is a section view diagram illustrating the orthotic knee control device (103), according to an embodiment as disclosed herein.

Referring to the FIG. 2, the orthotic knee control device (103) includes a non-return valve (201), an override button (202), a motor (203) that controls position of the valve, a motorized valve (204), a hydraulic piston rod wiper (205), a hydraulic piston (206), an accumulator piston (211), an accumulator chamber (207), a hydraulic chamber (208), and accumulator springs (212) including a primary spring (209) and a secondary spring (210). The accumulator chamber (207) is hydraulic.

In an embodiment, the hydraulic piston (206) is connected with the hydraulic chamber (208), the accumulator spring(s) is connected with the accumulator chamber (207), and the non-return valve (201) is connected in between the hydraulic chamber (208) and the accumulator chamber (207). The non-return valve (201) allows the flow of an oil from the accumulator chamber (207) to the hydraulic chamber (208) and does not allow the flow of the oil from the hydraulic chamber (208) to the accumulator chamber (207). Further, the orthotic knee control device (103) includes the motorized valve (204) that is connected between the hydraulic chamber (208) and the accumulator chamber (207). The motorized valve (204) controls the flow of oil based on one or more sensors. Examples of the motorized valve (204), include but not limited to, a pilot-operated servo valve, a solenoid valve, a non-motorized valve based on a pendulum and a flow rate control valve. Further, the accumulator springs (212) apply pressure to the hydraulic piston (206) via hydraulic fluid, to resist flexion of a knee joint and to aid extension of the knee joint.

In an embodiment, the oil flows from the hydraulic chamber (208) to the accumulator chamber (207) through the motorized valve (204) when a user flexes the knee joint. Further, the accumulator springs (212) are compressed when the user flexes the knee joint.

In an embodiment, the oil flows from the accumulator chamber (207) to the hydraulic chamber (208) through the motorized valve (204) and/or the non-return valve (201) when the user extends the knee joint.

In an embodiment, the oil flows from the accumulator chamber (207) to the hydraulic chamber (208) through the motorized valve (204) provides, but not limited to, a motion control in an extension direction, a control of extension damping during a swing and a stance extension adjustments.

In an embodiment, the motorized valve provides appropriate resistance to the user by controlling the flow of the oil based on the at least one sensor. The appropriate resistance prevents knee buckling. In an embodiment, adjusting the hydraulic resistance as flexion angle changes during stumbling, sitting, and stairs descent.

In an embodiment, the motorized valve provides high resistance to the user to provide support to the user when the user stumbles while the non-return valve allows the flow of the oil from the accumulator chamber to the hydraulic chamber.

Where during stumble recovery, the high resistance that opposes the knee flexing or bending allowing the user a chance or time to recover from a potential fall. In an embodiment, the resistance increases with increasing knee angles to offset the increase in the lever arm acting around the knee.

In an embodiment, the orthotic knee control device provides ease of movement without the usage of the motorized valve (204).

In an embodiment, the pressure from the accumulator springs (212) to the hydraulic piston (206) acts as a bias in extending the knee joint to support the users with lower limb paralysis, wherein the lower limb paralysis is due to includes, but not limited to, poliomyelitis nerve injuries, palsies and paraplegia.

In an embodiment, the orthotic knee control device (103) includes an override button (202), that allows the oil to flow from the accumulator chamber (207) to the hydraulic chamber (208) or from the hydraulic chamber (208) to the accumulator chamber (207) without using the motorized valve (204) and/or the non-return valve (201). Further, the override button (202) is used by the user when the motorized valve (204) and/or the non-return valve (201) is jammed or in the event of a power failure and the like.

In an embodiment, the override button (202) releases the knee joint to a pre-set resistance that is appropriate to the user or an environment. Further, the pre-set resistance selected by the user depends on the environment or activity of the user including, but not limited to cycling, sitting, and walking.

In an embodiment, the accumulator springs (212) are used in parallel with a hydraulic damper to allow realistic knee flexion with the extension bias to ensure that the orthosis (100) is in the correct position both during and at the end of swing phase.

In an embodiment, the proposed orthotic knee control device (103) has a range of interchangeable springs with different rates and adjustable pre-load, thus the orthosis (100) matches the amount of resistance and extension required for the user.

Figure 4A:
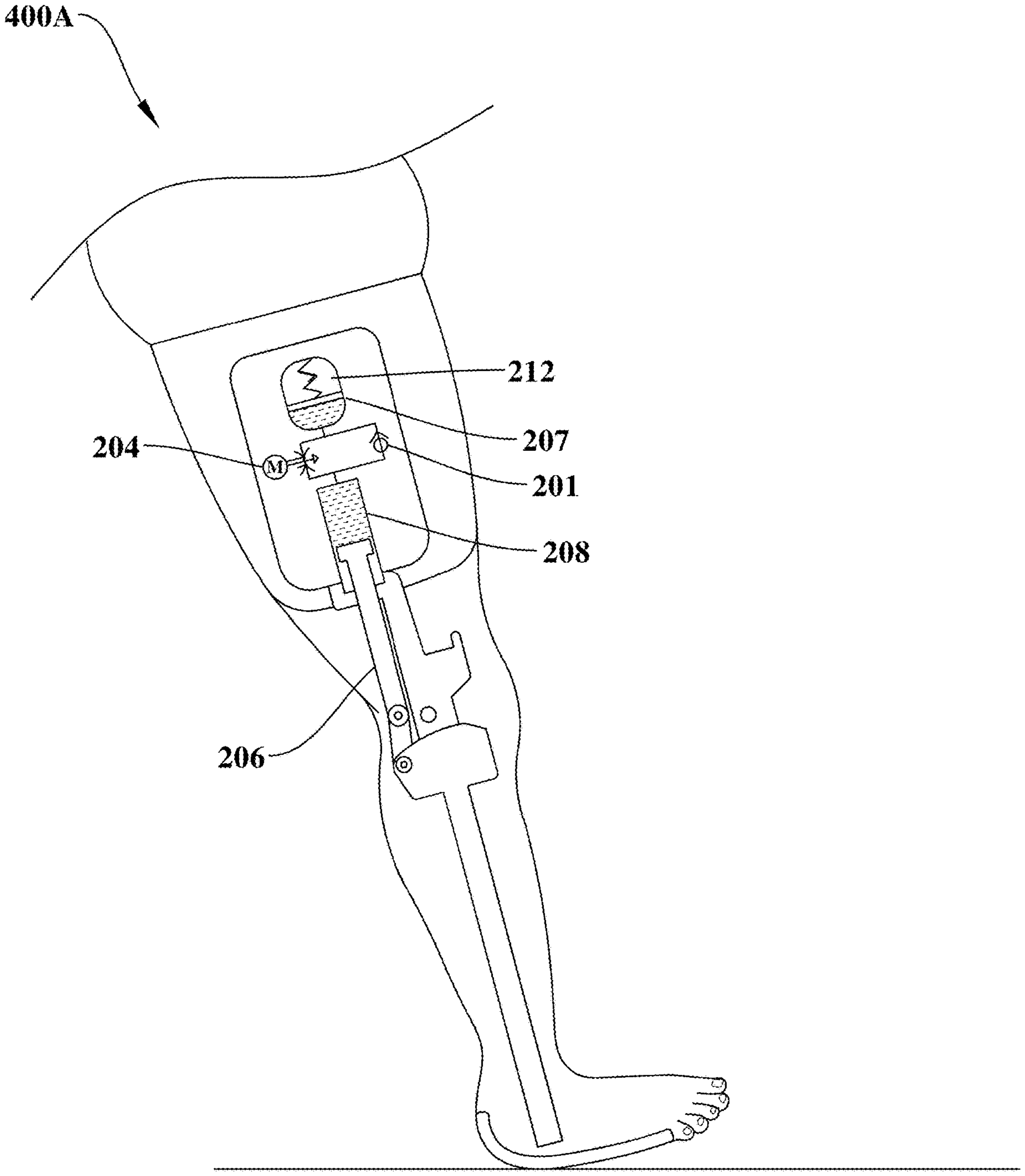
FIG. 4A is a schematic diagram illustrating a scenario of the orthosis when a heel makes contact with a ground, according to an embodiment as disclosed herein.
Figure 4B:
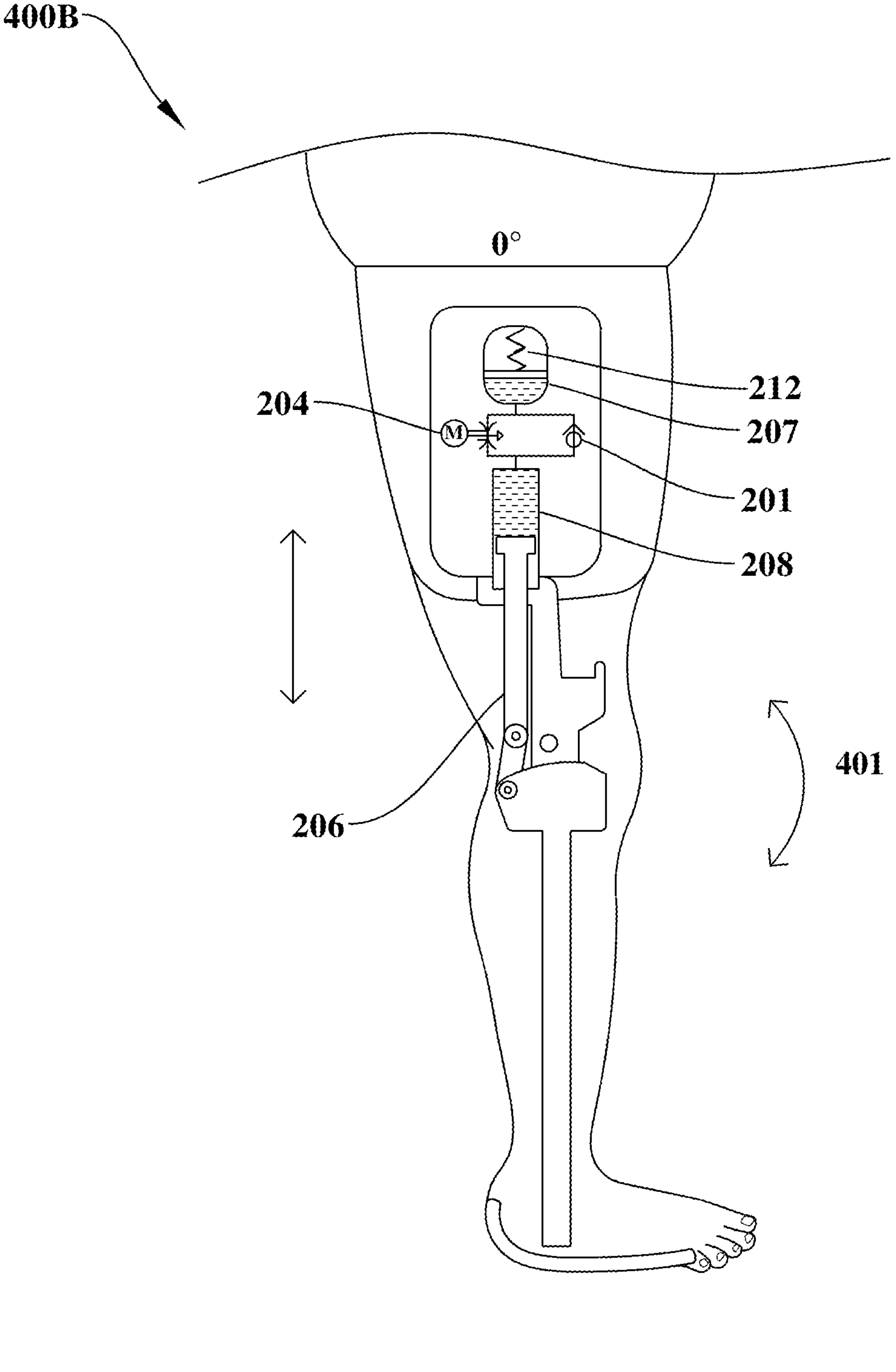
FIG. 4B is a schematic diagram illustrating a scenario of the orthosis when the flexion angle of a knee joint is zero, according to an embodiment as disclosed herein.
Figure 4C:
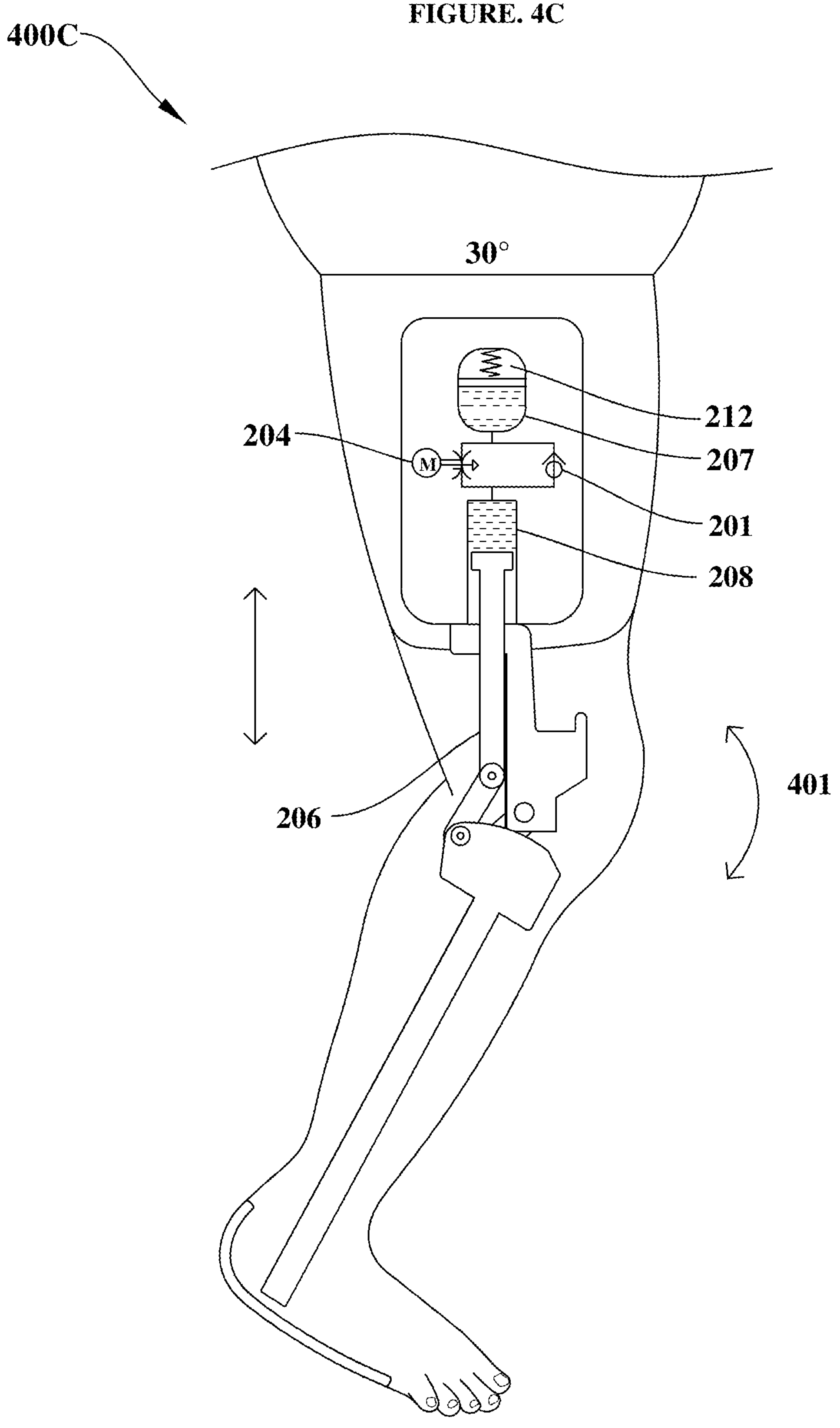
FIG. 4C is a schematic diagram illustrating a scenario of the orthosis when the flexion angle of the knee joint is thirty degrees, according to an embodiment as disclosed herein.
Figure 4D:
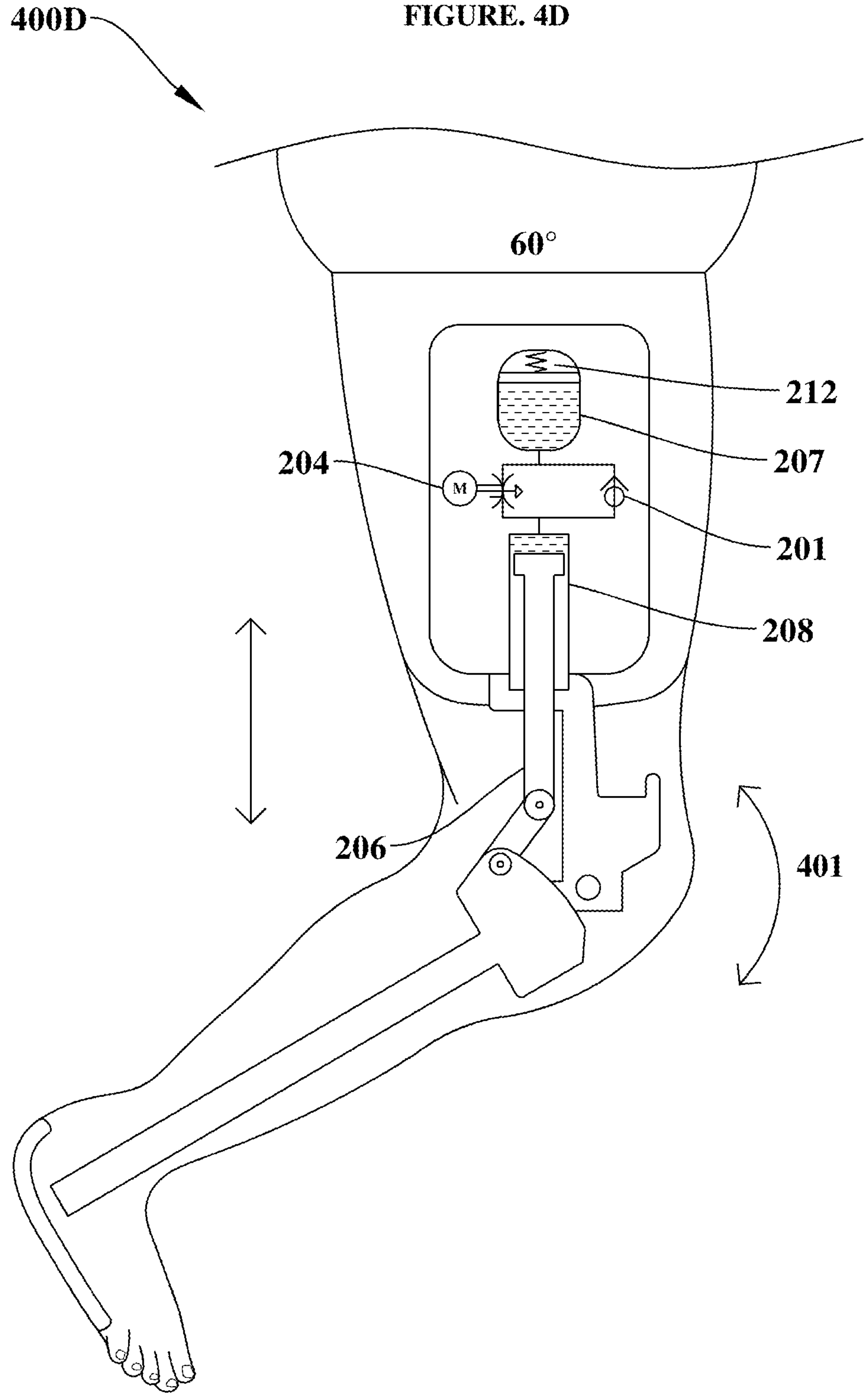
FIG. 4D is a schematic diagram illustrating a scenario of the orthosis when the flexion angle of the knee joint is sixty degrees, according to an embodiment as disclosed herein.

In an embodiment, for smaller flexion angles (i.e. when the flexion angle (401) is lesser than the threshold), the level of spring assist or resistance required is low to provide adequate ground clearance through the swing phase that is detailed in FIGS. 4C and 4D.

In an embodiment, the spring is designed in such a way that the rate is progressive depending on the amount of compression. The amount of compression is accomplished either by modifying the pitch of the coils in the spring or by the addition of a secondary spring (210) acting in series with the spring. The extension bias may also be achieved with a pneumatic piston or any other energy-storing or return means.

In an embodiment, a spring rate is progressive depending on the degree of compression. The spring rate is progressive by modifying the pitch of coils in the spring or by the addition of one or more secondary springs acting in series with the primary spring (209).

In an embodiment, the extension bias is achieved with a pneumatic piston or any other energy-storing or oil return valves or hybrid cylinder.

In an embodiment, the flexion and extension bias is adjusted according to, including but not limed to, individual user's requirements, limb length, weight of shoes, mechanical properties of the prosthetic leg (100) and inertia.

In an embodiment, the proposed orthotic knee control device (103) when used in the treatment of flaccid paralysis hydraulic damping with extension bias allows more realistic energy efficient gait and also helps to re-establish damaged neural pathways through repetitive motion.

Figure 3:
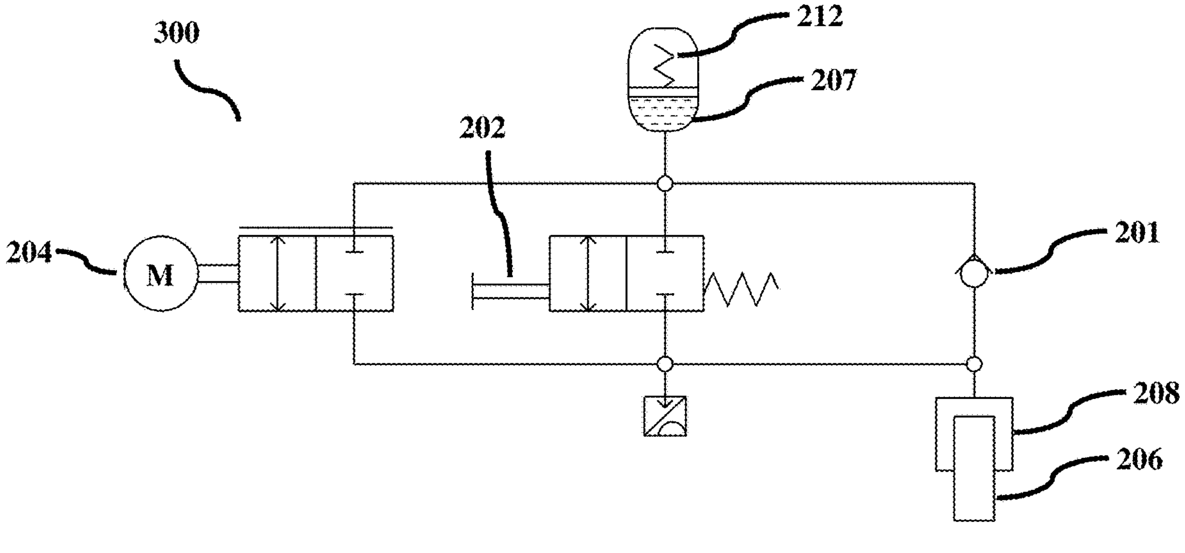
FIG. 3 is a schematic diagram illustrating a circuit diagram of the orthotic knee control device, according to an embodiment as disclosed herein.

FIG. 3 is a schematic diagram illustrating a circuit diagram (300) of the orthotic knee control device (103), according to an embodiment as disclosed herein.

In an embodiment, the accumulator springs (212) have a stiffness corresponding to a deflection. The deflection is low for an initial knee flexion that causes a stiffness of the accumulator springs (212) to be low. Further, an increase in the stiffness of the accumulator springs (212) when the deflection increases correspondingly increases flexion control and extension assistance includes, but not limited to, fast walking, sitting, and stair descent.

In an embodiment, the motorized valve (204) controls the flow of the oil based on one or more sensors includes, but not limited to, a pressure sensor, a foot force sensor, and kinematic sensors. Further, the one or more sensors determines includes, but not limited to, joint angles, velocities, and accelerations of the knee joint or a thigh segment.

In an embodiment, the motorized valve (204) is adjusted to provide, but not limited to, a required level of stance control, to provide free swing, and to adjust knee resistance suitable for, but not limited to, inclines, sitting and descent of stairs.

In an embodiment, the accumulator springs (212) are interchangeable springs that are interchanged with other springs based on the user's requirements to provide a degree of compression. Further, the degree of compression is performed by includes, but not limited to, modifying a pitch of coils of the accumulator springs (212) and adding one or more secondary springs (210) in addition to the primary spring (209). In an embodiment, the accumulator springs (212) is one or more variable rate springs, wherein the variable rate spring provides variable rate by varying the pitch in a single spring then allowing part of the single spring to become coil bound. The variable rate spring can also be referred as progressive rate springs.

In an embodiment, the primary spring and the secondary spring start to extend the knee joint when the knee joint is flexed to a maximum flexion angle, where the primary spring and the secondary spring extend the knee joint at a faster rate until the primary spring and the secondary spring return to their original lengths.

In an embodiment, the primary spring extends the knee joint at a slower rate to ensure that the knee joint is in the correct position. The extension of the stiffer secondary spring ensures a more rapid extension from maximum flexion angle until the flexion is as decompressed as possible. Further, the lower rate primary spring allows a more gentle extension over the last few degrees of extension producing a natural, comfortable deceleration into full knee extension.

In an embodiment, the degree of compression is modified by adjusting a pre-load of the accumulator springs (212).

In an embodiment, the accumulator springs (212) provide variable resistance to the flexion.

In an embodiment, the accumulator springs (212) are adjusted in the orthotic knee control device (103) according to the user requirements.

In an embodiment, the compression rate is comparatively low for smaller flexion angles, for example the initial compression rate is low for initial range (for example: 10-15 degrees) of flexion. The low compression rate helps with ground clearance to reduce a risk of tripping. During the flexion and extension, the compression rate of the one or more accumulator springs is higher for larger flexion angles. The higher compression rate helps control excessive heel rise whilst the extension bias helps ensure the knee is fully extended prior to a heel strike.

In an embodiment, during swing phase, the one or more accumulator springs allow easy initiation of knee flexion and knee bending with reduced user effort improving ground clearance in early swing phase. Further, when the flexion angle is larger, the secondary spring in conjunction with hydraulic damping controls excessive heel rise. Further, when the knee is flexed to a maximum flexion angle and inertia has been overcome, the one or more accumulator springs start to extend the limb. Initially at a faster rate when primary and secondary springs are returning to their natural length and at a lesser rate when the primary spring only is effective, ensuring the limb is in the correct position at the correct phase of gait. Thus the one or more accumulator springs improve ground clearance by controlling heel rise and extension rate of the knee. The proposed orthotic knee control device improves wearer safety and comfort during flexion and extension.

The geometry of the knee joint linkage is also an important consideration. This can affect not only the size of the device and the loads that are applied at the component level, but can also ensure that the movement of the piston at various stages of the gait is optimized in terms of hydraulic control.

The piston travel velocity is considered at various flexion angles in order to get support provided by the hydraulic chamber (208). Further, the piston travel velocity is considered to make it easier to control fine movements. In an embodiment, weight and size of the orthotic knee control device is optimized based on the user requirements.

In an embodiment, the springs are set up in the orthotic knee control device to bring change in stiffness according to the requirement of the user. The compression rate of the springs is proportional to the flexion angle (401).

In an embodiment, the orthotic knee control device (103) provides variable resistance to flexion, providing less resistance to initiation of knee flexion to improve ground clearance in an early swing in addition to aiding extension bias. Thus the one or more springs arrangement allows the extension bias that in conjunction with hydraulic resistance varies throughout extension.

FIG. 4A is a schematic diagram (400A) illustrating a scenario of the orthosis (100) when the heel makes contact with the ground, according to an embodiment as disclosed herein.

The orthosis (100) in the FIG. 4A discloses a scenario of a fully extended orthosis (100) at heel strike. When the orthosis (100) is fully extended, the oil that flowed from the accumulator chamber (207) to the hydraulic chamber (208) stays in the hydraulic chamber (208). Further, when the orthosis (100) is fully extended, the accumulator springs (212) contact the top of the accumulator chamber and apply lesser pressure to the hydraulic piston (206) as the flexion angle of the knee joint is lesser than the threshold.

When the orthosis (100) is fully extended before the heel strike, the motorized valve (204) is closed such that the knee is free to extend via oil flow. The oil flow through the non-return valve (201) that offers flexion support when required. When the flexion support is not required, the oil flow can be released by the override button (202) or based on the sensors in the orthosis (100).

When the orthosis (100) is fully extended before heel strike, the oil flows from the hydraulic chamber (208) to the accumulator chamber (207) through the motorized valve (204) to provide the motion control in the flexion direction, the swing, and the stance extension adjustments. The motorized valve (204) controls the flow of the oil based on various sensors, including but not limited to, the pressure sensor, the foot force sensor, and the kinematic sensors. Further, the one or more sensors determines the joint angles, velocities, and accelerations of the knee joint or the thigh segment FIG. 4B is a schematic diagram (400B) illustrating a scenario of the orthosis (100) when the flexion angle (401) of the knee joint is zero, according to an embodiment as disclosed herein.

The orthosis (100) in the FIG. 4B discloses a scenario of the fully extended limb in mid-stance. When the orthosis (100) is fully extended, the oil that flowed from the accumulator chamber (207) to the hydraulic chamber (208) stays in the hydraulic chamber (208). Further, when the orthosis (100) is fully extended, the accumulator springs (212) apply less pressure to the hydraulic piston (206) as the flexion angle (401) of the knee joint is less than the threshold.

In an embodiment, when the fully extended limb is in mid-stance, the motorized valve (204) is closed such that the knee is free to extend via oil flow. The oil flow through the non-return valve (201) offers flexion support when required. When the flexion support is not required, the oil flow can be released by the override button (202) or based on the sensors in the orthosis (100). Further, the motorized valve (204) is adjusted during various stages of stances or prior in heel strike to provide the required level of stance control.

FIG. 4C is a schematic diagram (400C) illustrating a scenario of the orthosis (100) when the flexion angle (401) of the knee joint is thirty degrees, according to an embodiment as disclosed herein.

In an embodiment, the accumulator springs (212) comprise the primary spring (209) and the secondary spring (210). The primary spring (209) applies pressure to the hydraulic piston (206) when the flexion angle (401) of the knee joint is below the threshold. The secondary spring (210) applies pressure to the hydraulic piston (206) when the flexion angle (401) of the knee joint is greater than the threshold.

In an embodiment, the flexion angle (401) is proportional to the compression rate of the accumulator springs (212).

In an embodiment, the flexion angle (401) and a hydraulic piston (206) travel velocity is considered for fine movements of the user.

In an embodiment, when the flexion angle (401) of the knee joint is thirty degrees during early swing, the oil flows from the hydraulic chamber (208) to the accumulator chamber (207) against the accumulator spring. The oil flows from the hydraulic chamber (208) to the accumulator chamber (207) through the motorized valve (204) when the user flexes the knee joint to thirty degrees.

When the user flexes the knee joint to thirty degrees, the accumulator springs (212) apply more pressure to the hydraulic piston (206) as the flexion angle (401) of the knee joint is above the threshold.

The flexion of the knee joint is significantly greater during swing (for example, flexion angle (401) is sixty degree) and lesser for (for example, flexion angle (401) is thirty degree). The flexion angle (401) is ninety degree when the user sits or decent of the stairs.

When the user flexes the knee joint from thirty degree to sixty degree or ninety degree flexion, the oil flows from the hydraulic chamber (208) to the accumulator chamber (207) through the motorized valve (204) providing a resistance to flexion of the knee joint.

In an embodiment, the flexion angle (401) is proportional to the compression rate of the accumulator springs (212). The compression of the accumulator springs (212) is lower when the knee is fully extended than when flexed to thirty degrees. The compression of the accumulator spring(s)

when flexed to thirty degrees is lower than the compression of the accumulator spring(s) at sixty degrees.

FIG. 4D is a schematic diagram (400D) illustrating a scenario of the orthosis (100) when the flexion angle (401) of the knee joint is sixty degrees, according to an embodiment as disclosed herein.

In an embodiment, when the user flexes the knee joint to sixty degrees, oil flows from the hydraulic chamber (208) to the accumulator chamber (207) against the accumulator spring. When the flexion angle (401) of the knee joint is sixty degrees the compression rate of the accumulator springs (212) is high as the flexion angle (401) is proportional to the compression rate of the accumulator springs (212). Furthermore, the oil in the hydraulic chamber (208) reduces and the oil in the accumulator chamber (207) increases as the flexion angle (401) increases.

In an embodiment, the higher compression rate bias helps the user to stand more easily from a sitting position. The higher compression rate helps overcome the hydraulics resistance.

The proposed orthotic knee control device (103) has two springs in series, the primary spring (209) has a low rate for small angular movements during stance or slow walking, and the secondary spring (210) has the higher rate becoming more dominant at larger flexion angles.

Spring stiffness increases during flexion and is greater at larger flexion angles. The greater stiffness helps control excessive heel rise whilst the extension bias helps ensure the knee is fully extended prior to heel strike.

In an embodiment, when the user flexes the knee joint to sixty degrees, the accumulator springs (212) apply higher pressure to the hydraulic piston (206) as the flexion angle (401) of the knee joint is above the threshold. The compression of the accumulator springs (212) is higher when the user flexes the knee joint to sixty degrees than at lower flexion angles.

The foregoing description of the specific embodiments reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within scope of the embodiments as described herein.

We claim:

1. An orthotic knee control device providing ease of movement, comprising:

a hydraulic piston connected with a hydraulic chamber;

at least one accumulator spring connected with an accumulator chamber;

a non-return valve connected between the hydraulic chamber and the accumulator chamber, wherein the non-return valve allows a flow of an oil from the accumulator chamber to the hydraulic chamber and does not allow the flow of the oil from the hydraulic chamber to the accumulator chamber; and a motorized valve connected between the hydraulic chamber and the accumulator chamber, wherein the motorized valve controls the flow of oil based on at least one sensor, and the at least one accumulator spring applies pressure to the hydraulic piston to resist flexion of a knee joint and to aid extension of the knee joint, wherein the at least one accumulator spring has a stiffness corresponding to a deflection, wherein the deflection is low for an initial knee flexion that causes a stiffness of the at least one accumulator spring to be low, and wherein increase in the stiffness of the at least one accumulator spring when the deflection increases correspondingly increasing at least one of flexion control and extension assistance comprising at least one of fast walking, sitting, and stair descent.

2. The orthotic knee control device as claimed in claim 1, wherein the at least one accumulator spring comprises at least one of a primary spring and a secondary spring, wherein the primary spring applies pressure to the hydraulic piston when a flexion angle of the knee joint is lesser than a threshold, wherein the secondary spring applies pressure to the hydraulic piston when the flexion angle of the knee joint is greater than the threshold.

3. The orthotic knee control device as claimed in claim 2, wherein the primary spring and the secondary spring start to extend the knee joint when the knee joint is flexed to a maximum flexion angle, wherein the primary spring and the secondary spring extend the knee joint at a faster rate till the primary spring and the secondary spring return to their original lengths;

wherein the primary spring extends the knee joint at a slower rate to at least one of avoiding the knee joint extending in an abrupt or aggressive manner and to smooth the extension.

4. The orthotic knee control device as claimed in claim 3, wherein the motorized valve provides appropriate resistance to the user by controlling the flow of the oil based on the at least one sensor, wherein the motorized valve provides high resistance to the user to provide support to the user when the user stumbles while the non-return valve allows the flow of the oil from the accumulator chamber to the hydraulic chamber.

5. The orthotic knee control device as claimed in claim 2, wherein the flexion angle is proportional to a compression rate of the at least one accumulator spring.

6. The orthotic knee control device as claimed in claim 1, comprises:

at least one override button, allowing the oil to flow from the accumulator chamber to the hydraulic chamber or from the hydraulic chamber to the accumulator chamber without using at least one the motorized valve and the non-return valve, wherein the at least one override button is used by the user when a quick release is required by the user or when at least one of the motorized valve and the non-return valve is at least one of jammed, during a power failure and malfunction.

7. The orthotic knee control device as claimed in claim 6, wherein the at least one override button releases the knee joint to a pre-set resistance, wherein the pre-set resistance is selected by the user depending on the environment or actions of the user comprising at least one of cycling, sitting, and walking.

8. The orthotic knee control device as claimed in claim 6, wherein the at least one override button comprises a plurality of positions for different levels of resistance.

9. The orthotic knee control device as claimed in claim 1, wherein the oil flows from the accumulator chamber to the hydraulic chamber through at least one of the motorized valve and the non-return valve when the user extends the knee joint.

10. The orthotic knee control device as claimed in claim 9, wherein the oil flows from the at least one of accumulator chamber to the hydraulic chamber and hydraulic chamber to accumulator chamber through the motorized valve providing at least one of: motion control in an extension direction, control of extension damping during swing and stance extension.

11. The orthotic knee control device as claimed in claim 1, wherein the at least one accumulator spring is interchangeable with other springs based on the user to provide a degree of compression, wherein the degree of compression is performed by at least one of modifying a pitch of coils in the at least one accumulator spring or adding at least one secondary spring along with the primary spring, wherein the at least one secondary spring is added in series with the primary spring.

12. The orthotic knee control device as claimed in claim 11, wherein the degree of compression is modified by adjusting a pre-load of the at least one accumulator spring.

13. The orthotic knee control device as claimed in claim 1, wherein the oil flows from the hydraulic chamber to the accumulator chamber through the motorized valve when a user flexes the knee joint, wherein the at least one accumulator spring is compressed when the user flexes the knee joint.

14. The orthotic knee control device as claimed in claim 1, wherein the pressure from the at least one accumulator spring to the hydraulic piston aids in extending the knee joint.

15. The orthotic knee control device as claimed in claim 1, wherein the motorized valve controls the flow of the oil based on the at least one sensor comprising at least one of a pressure sensor, a foot force sensor, and kinematic sensor, wherein the at least one sensor determines at least one of joint angles, velocities, and accelerations of the knee joint or a thigh segment.

16. The orthotic knee control device as claimed in claim 1, wherein the motorized valve is adjusted for at least one of to provide a required level of stance control, to provide free swing, and to make knee resistance suitable for at least one for sitting and descent of stairs.

17. The orthotic knee control device as claimed in claim 1, wherein the at least one accumulator spring provides variable resistance to the flexion or the extension of the knee joint.

18. The orthotic knee control device as claimed in claim 1, wherein the flexion angle and a hydraulic piston travel velocity are considered for fine movements of the user.

* * * * *